United States Patent [19]

Leissing et al.

[11] Patent Number: 5,281,396
[45] Date of Patent: * Jan. 25, 1994

[54] AUTOMATED TEST SYSTEM FOR EVALUATING THE PHYSICAL COMPATIBILITY OF INTRAVENOUS DRUGS IN SOLUTIONS

[75] Inventors: Nancy C. Leissing, Lake Forest; Diana Oskroba, McHenry, both of Ill.

[73] Assignee: Baxter International Inc., Deerfield, Ill.

[*] Notice: The portion of the term of this patent subsequent to Feb. 4, 2009 has been disclaimed.

[21] Appl. No.: 734,624

[22] Filed: Jul. 23, 1991

Related U.S. Application Data

[62] Division of Ser. No. 445,234, Dec. 1, 1989, Pat. No. 5,086,001.

[51] Int. Cl.$^5$ ............... G01N 21/84; G01N 21/90
[52] U.S. Cl. ............... 422/82.09; 422/67; 422/82.05; 356/319; 364/498
[58] Field of Search ............... 422/62, 63–67, 422/68.1, 81, 82.05, 82.09; 356/319, 334; 364/498

[56] References Cited

U.S. PATENT DOCUMENTS

| | | | |
|---|---|---|---|
| 3,833,304 | 9/1974 | Liston | 356/184 |
| 4,067,775 | 1/1978 | Wurzburg et al. | 195/99 |
| 4,102,747 | 7/1978 | Driscoll et al. | 195/103.5 |
| 4,429,373 | 1/1984 | Fletcher et al. | 364/900 |
| 4,451,563 | 5/1984 | Kaufman | 435/21 |
| 4,477,190 | 10/1984 | Liston et al. | 356/418 |
| 4,528,159 | 7/1985 | Liston | 422/65 |
| 4,595,562 | 7/1986 | Liston et al. | 422/65 |
| 4,668,617 | 5/1987 | Furuta et al. | 435/4 |
| 4,669,878 | 6/1987 | Meier | 356/319 |
| 4,687,962 | 8/1987 | Elbert | 310/316 |
| 4,767,716 | 8/1988 | Sakamaki et al. | 436/47 |
| 4,871,682 | 10/1989 | Mazza | 436/179 |
| 4,980,292 | 12/1990 | Elbert et al. | 435/289 |

FOREIGN PATENT DOCUMENTS 1229292 11/1987 Canada ................... 150/3

OTHER PUBLICATIONS

Paramax Analytical System.
Yalkowsky et al., "In Vitro Method for Detecting Precipitation of Parenteral Formulations After Injection," *Journal of Pharmaceutical Sciences*, vol. 72(9) pp. 1014–1017 (1983).
Dasta et al., "Comparison of Visual Turbidimetric Methods for Determining Short-Term Compatibility of

(List continued on next page.)

*Primary Examiner*—James C. Housel
*Assistant Examiner*—David Redding
*Attorney, Agent, or Firm*—Paul E. Schaafsma; Amy L. H. Rockwell; Paul C. Flattery

[57] ABSTRACT

A system for evaluating the physical compatibility of two or more pharmaceutical chemicals in solution mixes chemical solutions in predetermined relative quantities in a test well and, under the direction of a control mechanism, measures the absorption of the mixture at two different wavelengths. The first wavelength is within the visual spectrum in the range of 400 to 500 nm and detects both changes in color and changes in physical properties caused by mixing the chemical solutions. The second wavelength is above the visual spectrum in the range of 610 to 650 nm to detect only changes in physical properties caused by mixing the chemical solutions. The control mechanism further compares the absorption measured at the two different wavelengths to differentiate between solely color changes and physical property changes (with or without color changes) caused by the mixing. The control mechanism also provides an output of the differentiated results.

1 Claim, 8 Drawing Sheets

OTHER PUBLICATIONS

Intravenous Critical Care Drugs", *American Journal of Hospital Pharmacy*, vol. 45, pp. 2361-2366 (1988).

Bogash, "Compatibilities and Incompatibilities of Some Parenteral Medication," *American Society of Hospital Pharmacists*, vol. 12, pp. 445-448 (1955).

Marquardt, "Visual Compatibility of Tolazoline Hydrochloride With Various Medications During Simulated Y-Site Injection," *American Journal of Hospital Pharmacy*, vol. 47, pp. 1802-1803 (Aug., 1990).

Baltz et al., "Visual Compatibility of Foscarnet With Other Injectable Drugs During Simulated Y-Site Administration", *American Journal of Hospital Pharmacy*, vol. 47, pp. 2075-2077 (Sep., 1990).

Bing et al., "Compatibility of Critical Care Drip Medication: Where is the Information?", *Infusion*, pp. 118-120 (Jul./Aug. 1982).

Lee et al., "Visual and Spectrophotometric Determination of Compatibility of Alteplase and Streptokinase with Other Injectable Drugs," *American Journal of Hospital Pharmacy*, vol. 47, pp. 606-608 (1990).

Biomek 1000 Trade Brochure; Copyright 1986.

EAR 4000/340 AT Trade Brochure; Copyright 1987.

Clinical Chemistry; Theory, Analysis, and Correlation; Lawrence A. Kaplan et al., The CV Mosby Co., 2nd Edition, 1989.

FIG.1A

| DRUG | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | No |
|---|---|---|---|---|---|---|---|---|---|---|---|---|---|---|---|---|---|---|---|---|---|---|---|---|---|
| Amikacin | xxx | | | | | | | | | | | | | | | | | | | | | | | | 1 |
| Gentamicin | x | xxx | | | | | | | | | | | | | | | | | | | | | | | 2 |
| Tobramycin | x | x | xxx | | | | | | | | | | | | | | | | | | | | | | 3 |
| Amphotericin B | x | x | x | xxx | | | | | | | | | | | | | | | | | | | | | 4 |
| Cefazolin | x | x | x | x | xxx | | | | | | | | | | | | | | | | | | | | 5 |
| Ceftriaxone | x | x | x | x | x | xxx | | | | | | | | | | | | | | | | | | | 6 |
| Cefotaxime | x | x | x | x | x | x | xxx | | | | | | | | | | | | | | | | | | 7 |
| Ceftizoxime | x | x | x | x | x | x | x | xxx | | | | | | | | | | | | | | | | | 8 |
| Cefuroxime | x | x | x | x | x | x | x | x | xxx | | | | | | | | | | | | | | | | 9 |
| Ceftazidime | x | x | x | x | x | x | x | x | x | xxx | | | | | | | | | | | | | | | 10 |
| Cefoxitin | x | x | x | x | x | x | x | x | x | x | xxx | | | | | | | | | | | | | | 11 |
| Cefotetan | x | x | x | x | x | x | x | x | x | x | x | xxx | | | | | | | | | | | | | 12 |
| Erythromycin Lactobionate | x | x | x | x | x | x | x | x | x | x | x | x | xxx | | | | | | | | | | | | 13 |
| Ampicillin | x | x | x | x | x | x | x | x | x | x | x | x | x | xxx | | | | | | | | | | | 14 |
| Penicillin G Potassium | x | x | x | x | x | x | x | x | x | x | x | x | x | x | xxx | | | | | | | | | | 15 |
| Piperacillin | x | x | x | x | x | x | x | x | x | x | x | x | x | x | x | xxx | | | | | | | | | 16 |
| Ticarcillin | x | x | x | x | x | x | x | x | x | x | x | x | x | x | x | x | xxx | | | | | | | | 17 |
| Nafcillin Sodium | x | x | x | x | x | x | x | x | x | x | x | x | x | x | x | x | x | xxx | | | | | | | 18 |
| Clindamycin | x | x | x | x | x | x | x | x | x | x | x | x | x | x | x | x | x | x | xxx | | | | | | 19 |
| Vancomycin | x | x | x | x | x | x | x | x | x | x | x | x | x | x | x | x | x | x | x | xxx | | | | | 20 |
| Trimethoprim/Sulfate Thoxazole | x | x | x | x | x | x | x | x | x | x | x | x | x | x | x | x | x | x | x | x | xxx | | | | 21 |
| Metronidazole | x | x | x | x | x | x | x | x | x | x | x | x | x | x | x | x | x | x | x | x | x | xxx | | | 22 |
| Dobutamine | x | x | x | x | x | x | x | x | x | x | x | x | x | x | x | x | x | x | x | x | x | x | xxx | | 23 |
| Norepinephrine | x | x | x | x | x | x | x | x | x | x | x | x | x | x | x | x | x | x | x | x | x | x | x | xxx | 24 |

FIG. 1B

| DRUG | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | No |
|---|---|---|---|---|---|---|---|---|---|---|---|---|---|---|---|---|---|---|---|---|---|---|---|---|---|
| Amikacin | | | | | | | | | | | | c | | c | | | | | c | | | | | | 1 |
| Gentimicin | | | | | | | | | | | | c | | c | | | | | - | | | | | | 2 |
| Tobramycin | | | | | | | | | | | | c | | c | | | | | c | | | | | | 3 |
| Amphotericin ? | | | | | | | | | | | | | | | | | | | | | | | | | 4 |
| Cefazolin | | | | | | | | | | | | c | | c | | | | | | | | | | | 5 |
| Ceftriaxone | | | c | | | | | | | | | | | | | | | | | | | | | | 6 |
| Cefotaxime | | | | | | | | | | | | c | | c | | | | | | | | | | | 7 |
| Cefizoxime | | | | | | | | | | | | c. | | | | | | | | | | | | | 8 |
| Cefuroxime | | | | | | | | | | | | c | | c | | | | | | | | | | | 9 |
| Ceftazidime | | | | | | | | | | | | | | | | | | | | | | | | | 10 |
| Cefoxitin | | | c | | | | | | | | | c | | c | | | | | | | | | | | 11 |
| Cefotetam | | | | | | | | | | | | | | | | | | | | | | | | | 12 |
| Erythromycin Lactobionate | | | | | | | | | | | | c | | c | | | | | | | | | | | 13 |
| Ampicillin | | | c | | | | | | | | | c | | c | | c | | | | | | | c | | 14 |
| Penicillin G Potassium | | | c | | | | | | | | | c | | c | | c | | | | | | | c | | 15 |
| Piperacillin | | | | | | | | | | | | c | | c | | | | | | | | | | | 16 |
| Ticarcillin | | | | | | | | | | | | c | | | | | | | | | | | | | 17 |
| Nafcillin Sodium | | | | | | | | - | | | | c | | c | | | | | | | | | | | 18 |
| Clindamycin | | | | | | | | | | | | c | | c | | | | | | | | | | | 19 |
| Vancomycin | | | | | | | | | | | | c | | c | | | | | | | | | | | 20 |
| Trimethoprim/Sulfate Thoxazole | | | c | | | | | | | | | c | | c | | | | | | | | | | | 21 |
| Metronipazole | | | | | | | | | | | | c | | | | | | | | | | | | | 22 |
| Dobutamine | | | | | | | | | | | | | | | | c | | | | | | | | | 23 |
| Norepinephrine | | | c | | | | | | | | | | | | | | | | | | | | c | | 24 |

FIG. 1C

| DRUG | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | No |
|---|---|---|---|---|---|---|---|---|---|---|---|---|---|---|---|---|---|---|---|---|---|---|---|---|---|
| Dopamine | x | x | x | x | x | x | x | x | x | x | x | x | x | x | x | x | x | x | x | x | x | x | x | x | 25 |
| Isoproterewol | x | x | x | x | x | x | x | x | x | x | x | x | x | x | x | x | x | x | x | x | x | x | x | x | 26 |
| Heparin Sodium | x | x | x | x | x | x | x | x | x | x | x | x | x | x | x | x | x | x | x | x | x | x | x | x | 27 |
| Propranolol | x | x | x | x | x | x | x | x | x | x | x | x | x | x | x | x | x | x | x | x | x | x | x | x | 28 |
| Bretylium | x | x | x | x | x | x | x | x | x | x | x | x | x | x | x | x | x | x | x | x | x | x | x | x | 29 |
| Lidocaine | x | x | x | x | x | x | x | x | x | x | x | x | x | x | x | x | x | x | x | x | x | x | x | x | 30 |
| Digoxin | x | x | x | x | x | x | x | x | x | x | x | x | x | x | x | x | x | x | x | x | x | x | x | x | 31 |
| Verapamil | x | x | x | x | x | x | x | x | x | x | x | x | x | x | x | x | x | x | x | x | x | x | x | x | 32 |
| Sodium Nitroprusside | x | x | x | x | x | x | x | x | x | x | x | x | x | x | x | x | x | x | x | x | x | x | x | x | 33 |
| Hydralazine | x | x | x | x | x | x | x | x | x | x | x | x | x | x | x | x | x | x | x | x | x | x | x | x | 34 |
| Nitroglycerin | x | x | x | x | x | x | x | x | x | x | x | x | x | x | x | x | x | x | x | x | x | x | x | x | 35 |
| Morphine Sulfate | x | x | x | x | x | x | x | x | x | x | x | x | x | x | x | x | x | x | x | x | x | x | x | x | 36 |
| Phenytoin | x | x | x | x | x | x | x | x | x | x | x | x | x | x | x | x | x | x | x | x | x | x | x | x | 37 |
| Magnesium Sulfate | x | x | x | x | x | x | x | x | x | x | x | x | x | x | x | x | x | x | x | x | x | x | x | x | 38 |
| Sodium Bicarbonate | x | x | x | x | x | x | x | x | x | x | x | x | x | x | x | x | x | x | x | x | x | x | x | x | 39 |
| Potassium Chloride | x | x | x | x | x | x | x | x | x | x | x | x | x | x | x | x | x | x | x | x | x | x | x | x | 40 |
| Calcium Gluconate | x | x | x | x | x | x | x | x | x | x | x | x | x | x | x | x | x | x | x | x | x | x | x | x | 41 |
| Calcium Chloride | x | x | x | x | x | x | x | x | x | x | x | x | x | x | x | x | x | x | x | x | x | x | x | x | 42 |
| Furosenide | x | x | x | x | x | x | x | x | x | x | x | x | x | x | x | x | x | x | x | x | x | x | x | x | 43 |
| Mannitol | x | x | x | x | x | x | x | x | x | x | x | x | x | x | x | x | x | x | x | x | x | x | x | x | 44 |
| Cimetidine | x | x | x | x | x | x | x | x | x | x | x | x | x | x | x | x | x | x | x | x | x | x | x | x | 45 |
| Ranitidine | x | x | x | x | x | x | x | x | x | x | x | x | x | x | x | x | x | x | x | x | x | x | x | x | 46 |
| Hydrocortisone (Sod. Succinate) | x | x | x | x | x | x | x | x | x | x | x | x | x | x | x | x | x | x | x | x | x | x | x | x | 47 |
| Human Insulin | x | x | x | x | x | x | x | x | x | x | x | x | x | x | x | x | x | x | x | x | x | x | x | x | 48 |

FIG. 1D

| DRUG | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | No |
|---|---|---|---|---|---|---|---|---|---|---|---|---|---|---|---|---|---|---|---|---|---|---|---|---|---|
| Dopamine | xxx | | c | | | | | c | | | | | | | | c | | | | | | | c | | 25 |
| Isoproterewol | x | xxx | c | | | | | | | | | | | | | c | | | | | | | c | | 26 |
| Heparin Sodium | x | x | xxx | c | | c | c | | | c | | c | | c | c | | c | | c | | c | | | | 27 |
| Propranolol | x | x | x | xxx | | | | | | | | | | | | c | | | | | | | c | | 28 |
| Bretylium | x | x | x | x | xxx | | | | | | | | | | | | | | | | | | | | 29 |
| Lidocaine | x | x | x | x | x | xxx | | | | | | | | | | c | | | | | | | | | 30 |
| Digoxin | x | x | x | x | x | x | xxx | | | | | | | | | c | | | | | | | c | | 31 |
| Verapamil | x | x | x | x | x | x | x | xxx | | | | | | | i | | | | | | | | | | 32 |
| Sodium Nitroprusside | x | x | x | x | x | x | x | x | xxx | | | | | | | | | | | | | | | | 33 |
| Hydralazine | x | x | x | x | x | x | x | x | x | xxx | | | | | | c | | | | | | | c | | 34 |
| Nitroglycerin | x | x | x | x | x | x | x | x | x | x | xxx | | | | | | | | | | | | | | 35 |
| Morphine Sulfate | x | x | x | x | x | x | x | x | x | x | x | xxx | | | | c | | | | | | | c | | 36 |
| Phenytoin | x | x | x | x | x | x | x | x | x | x | x | x | xxx | | | i | | | | | | | i | | 37 |
| Magnesium Sulfate | x | x | x | x | x | x | x | x | x | x | x | x | x | xxx | | c | | | | | | | c | | 38 |
| Sodium Bicarbonate | x | x | x | x | x | x | x | x | x | x | x | x | x | x | xxx | c | | | | | | | c | | 39 |
| Potassium Chloride | x | x | x | x | x | x | x | x | x | x | x | x | x | x | x | xxx | c | | c | | | | | | 40 |
| Calcium Glucomate | x | x | x | x | x | x | x | x | x | x | x | x | x | x | x | x | xxx | | | | | | | | 41 |
| Calcium Chloride | x | x | x | x | x | x | x | x | x | x | x | x | x | x | x | x | x | xxx | | | | | c | | 42 |
| Furosenide | x | x | x | x | x | x | x | x | x | x | x | x | x | x | x | x | x | x | xxx | | | | c | | 43 |
| Manmitol | x | x | x | x | x | x | x | x | x | x | x | x | x | x | x | x | x | x | x | xxx | | | | | 44 |
| Cimetidine | x | x | x | x | x | x | x | x | x | x | x | x | x | x | x | x | x | x | x | x | xxx | | | | 45 |
| Ranitidine | x | x | x | x | x | x | x | x | x | x | x | x | x | x | x | x | x | x | x | x | x | xxx | | | 46 |
| Hydrocortisone (Sod. Succinate) | x | x | x | x | x | x | x | x | x | x | x | x | x | x | x | x | x | x | x | x | x | x | xxx | | 47 |
| Human Insulin | x | x | x | x | x | x | x | x | x | x | x | x | x | x | x | x | x | x | x | x | x | x | x | xxx | 48 |

|   | 1 | 2 | 3 | 4 | 5 | 6 | 7 | 8 | 9 | 10 | 11 | 12 |
|---|---|---|---|---|---|---|---|---|---|---|---|---|
| A | VEHICLE BLANK | CHEM 1 + VEHICLE | CHEM 1 + Chem 1 | CHEM 1 + Chem 2 | CHEM 1 + Chem 3 | CHEM 1 + Chem 4 | CHEM 1 + Chem 5 | CHEM 1 + Chem 6 | CHEM 1 + Chem 7 | CHEM 1 + Chem 8 | 0.02%NaCl + 0.02%AgNO3 | |
| B | VEHICLE BLANK | CHEM 2 + VEHICLE | CHEM 2 + Chem 1 | CHEM 2 + Chem 2 | CHEM 2 + Chem 3 | CHEM 2 + Chem 4 | CHEM 2 + Chem 5 | CHEM 2 + Chem 6 | CHEM 2 + Chem 7 | CHEM 2 + Chem 8 | 1:2 NaCl + 1:2 AgNO3 | |
| C | VEHICLE BLANK | CHEM 3 + VEHICLE | CHEM 3 + Chem 1 | CHEM 3 + Chem 2 | CHEM 3 + Chem 3 | CHEM 3 + Chem 4 | CHEM 3 + Chem 5 | CHEM 3 + Chem 6 | CHEM 3 + Chem 7 | CHEM 3 + Chem 8 | 1:4 NaCl + 1:4 AgNO3 | |
| D | VEHICLE BLANK | CHEM 4 + VEHICLE | CHEM 4 + Chem 1 | CHEM 4 + Chem 2 | CHEM 4 + Chem 3 | CHEM 4 + Chem 4 | CHEM 4 + Chem 5 | CHEM 4 + Chem 6 | CHEM 4 + Chem 7 | CHEM 4 + Chem 8 | 1:8 NaCl + 1:8 AgNO3 | |
| E | VEHICLE BLANK | CHEM 5 + VEHICLE | CHEM 5 + Chem 1 | CHEM 5 + Chem 2 | CHEM 5 + Chem 3 | CHEM 5 + Chem 4 | CHEM 5 + Chem 5 | CHEM 5 + Chem 6 | CHEM 5 + Chem 7 | CHEM 5 + Chem 8 | 1:16 NaCl + 1:16 AgNO3 | |
| F | VEHICLE BLANK | CHEM 6 + VEHICLE | CHEM 6 + Chem 1 | CHEM 6 + Chem 2 | CHEM 6 + Chem 3 | CHEM 6 + Chem 4 | CHEM 6 + Chem 5 | CHEM 6 + Chem 6 | CHEM 6 + Chem 7 | CHEM 6 + Chem 8 | 1:32 NaCl + 1:32 AgNO3 | |
| G | VEHICLE BLANK | CHEM 7 + VEHICLE | CHEM 7 + Chem 1 | CHEM 7 + Chem 2 | CHEM 7 + Chem 3 | CHEM 7 + Chem 4 | CHEM 7 + Chem 5 | CHEM 7 + Chem 6 | CHEM 7 + Chem 7 | CHEM 7 + Chem 8 | 0.02% Latex | |
| H | VEHICLE BLANK | CHEM 8 + VEHICLE | CHEM 8 + Chem 1 | CHEM 8 + Chem 2 | CHEM 8 + Chem 3 | CHEM 8 + Chem 4 | CHEM 8 + Chem 5 | CHEM 8 + Chem 6 | CHEM 8 + Chem 7 | CHEM 8 + Chem 8 | 0.02% Latex | |

FIG. 2

|   | 1 | 2 | 3 | 4 | 5 | 6 | 7 | 8 | 9 | 10 | 11 | 12 |
|---|---|---|---|---|---|---|---|---|---|---|---|---|
| A | VEHICLE BLANK | CHEM 1 + VEHICLE | CHEM 1 + Chem 9 | CHEM 1 + Chem 10 | CHEM 1 + Chem 11 | CHEM 1 + Chem 12 | CHEM 1 + Chem 13 | CHEM 1 + Chem 14 | CHEM 1 + Chem 15 | CHEM 1 + Chem 16 | 0.02%NaCl + 0.02%AgNO3 | Chem 9 + VEHICLE |
| B | VEHICLE BLANK | CHEM 2 + VEHICLE | CHEM 2 + Chem 9 | CHEM 2 + Chem 10 | CHEM 2 + Chem 11 | CHEM 2 + Chem 12 | CHEM 2 + Chem 13 | CHEM 2 + Chem 14 | CHEM 2 + Chem 15 | CHEM 2 + Chem 16 | 1:2 NaCl + 1:2 AgNO3 | Chem 10 + VEHICLE |
| C | VEHICLE BLANK | CHEM 3 + VEHICLE | CHEM 3 + Chem 9 | CHEM 3 + Chem 10 | CHEM 3 + Chem 11 | CHEM 3 + Chem 12 | CHEM 3 + Chem 13 | CHEM 3 + Chem 14 | CHEM 3 + Chem 15 | CHEM 3 + Chem 16 | 1:4 NaCl + 1:4 AgNO3 | Chem 11 + VEHICLE |
| D | VEHICLE BLANK | CHEM 4 + VEHICLE | CHEM 4 + Chem 9 | CHEM 4 + Chem 10 | CHEM 4 + Chem 11 | CHEM 4 + Chem 12 | CHEM 4 + Chem 13 | CHEM 4 + Chem 14 | CHEM 4 + Chem 15 | CHEM 4 + Chem 16 | 1:8 NaCl + 1:8 AgNO3 | Chem 12 + VEHICLE |
| E | VEHICLE BLANK | CHEM 5 + VEHICLE | CHEM 5 + Chem 9 | CHEM 5 + Chem 10 | CHEM 5 + Chem 11 | CHEM 5 + Chem 12 | CHEM 5 + Chem 13 | CHEM 5 + Chem 14 | CHEM 5 + Chem 15 | CHEM 5 + Chem 16 | 1:16 NaCl + 1:16 AgNO3 | Chem 13 + VEHICLE |
| F | VEHICLE BLANK | CHEM 6 + VEHICLE | CHEM 6 + Chem 9 | CHEM 6 + Chem 10 | CHEM 6 + Chem 11 | CHEM 6 + Chem 12 | CHEM 6 + Chem 13 | CHEM 6 + Chem 14 | CHEM 6 + Chem 15 | CHEM 6 + Chem 16 | 1:32 NaCl + 1:32 AgNO3 | Chem 14 + VEHICLE |
| G | VEHICLE BLANK | CHEM 7 + VEHICLE | CHEM 7 + Chem 9 | CHEM 7 + Chem 10 | CHEM 7 + Chem 11 | CHEM 7 + Chem 12 | CHEM 7 + Chem 13 | CHEM 7 + Chem 14 | CHEM 7 + Chem 15 | CHEM 7 + Chem 16 | 0.02% Latex | Chem 15 + VEHICLE |
| H | VEHICLE BLANK | CHEM 8 + VEHICLE | CHEM 8 + Chem 9 | CHEM 8 + Chem 10 | CHEM 8 + Chem 11 | CHEM 8 + Chem 12 | CHEM 8 + Chem 13 | CHEM 8 + Chem 14 | CHEM 8 + Chem 15 | CHEM 8 + Chem 16 | 0.02% Latex | Chem 16 + VEHICLE |

| Drug Combination | INITIAL | | 1 HOUR | | 3 HOUR | | DECISION |
|---|---|---|---|---|---|---|---|
| | 450nm | 620nm | 450nm | 620nm | 450nm | 620nm | |
| Amikacin +<br>Furosemide | 0.000<br>0.006 | 0.002<br>0.009 | 0.000<br>0.007 | 0.006<br>0.012 | 0.000<br>0.012 | 0.006<br>0.014 | COMPATIBLE |
| Gentamicin +<br>Furosemide | 1.800<br>1.698 | 1.632<br>1.707 | 0.855<br>0.482 | 0.860<br>0.501 | 0.310<br>0.184 | 0.305<br>0.172 | INCOMPATIBLE:<br>Precipitate in Both Directions |
| Gentamicin +<br>Folic Acid | 0.188<br>0.202 | 0.042<br>0.053 | 0.334<br>0.202 | 0.054<br>0.049 | 0.347<br>0.222 | 0.058<br>0.057 | INCOMPATIBLE:<br>Precipitate and Green Color |
| Cefazolin +<br>Erythromycin | 0.004<br>0.007 | 0.007<br>0.005 | 0.004<br>0.220 | 0.006<br>0.182 | 0.003<br>0.032 | 0.009<br>0.033 | INCOMPATIBLE:<br>Transient Precipitate in One Direction Only |
| Ceftizoxime +<br>Chloramphenicol | 0.301<br>0.355 | 0.014<br>0.003 | 0.350<br>0.378 | 0.008<br>0.005 | 0.414<br>0.485 | 0.012<br>0.005 | INCOMPATIBLE:<br>Yellow Color |
| Gentamicin +<br>Cefotetan | 0.731<br>0.007 | 0.722<br>0.021 | 0.011<br>0.000 | 0.020<br>0.012 | 0.005<br>0.000 | 0.018<br>0.012 | INCOMPATIBLE:<br>Transient Precipitate in One Direction Only |

Fig. 5

AUTOMATED TEST SYSTEM FOR EVALUATING THE PHYSICAL COMPATIBILITY OF INTRAVENOUS DRUGS IN SOLUTIONS

This is a divisional of copending application Ser. No. 07/445,234 filed on Dec. 1, 1989, now U.S. Pat. No. 5,086,001.

FIELD OF THE INVENTION

The present invention relates to evaluating the physical compatibility of chemicals in solution. More specifically, this invention pertains to an automated, high volume process for detecting, identifying and quantifying physical incompatibility reactions resulting from mixing at least two chemicals in solution.

BACKGROUND OF THE INVENTION

Within the scope of current medical care and especially in the Intensive Care Unit (ICU), concern for inter-drug compatibility has always been a matter of life-and-death proportion. The compatibility of chemicals, especially drugs, with one another in solution generally includes many factors such as physical compatibility of the chemicals and the diluent employed, chemical stability, chemical interactions and absorption issues. Indications of physical incompatibility include the formation of haze, turbidity, precipitate, crystals and globules. The present invention relates to physical compatibility.

Intravenous drug and solution compatibility testing, at least from the standpoint of physical compatibility, began over 30 years ago. In 1955, R. Bogash published an article, "Compatibilities and Incompatibilities in Some Parenteral Medications" in a bulletin from the American Society of Hospital Pharmacists (12:455–488, July-Aug., 1955). Since then, there has been a substantial body of literature on the subject of intravenous compatibility. One of the largest studies ever performed was published by Kirkland, et al, entitled, Compatibility Studies of Parenterals Admixtures, in the American Journal of Hospital Pharmacy (18:694–699, Dec, 1961). It reported physical compatibility results for about 4,000 combinations of 68 drug combinations diluted in 59 infusion solutions. To date, this is the largest study published on physical compatibility results.

Another major study by Patel and Phillips (kn. J. Hosp. Pharm., 23:409–411, 1966) reported results on about 3,000 drug combinations. In addition to these major studies, there are over 1,000 other articles on drug compatibility published to date.

Generally speaking, the more serious a patient's condition, the more drugs the patient will be receiving. The average number of drugs per patient administered in a typical ICU is 10–12 per day. These drugs usually are administered at 2–4 delivery doses per day, for a total of 20–48 drug doses per day. This number is exclusive of other required fluids and nutritional solutions. It is not uncommon for patients to receive 50–70 drug doses per day and there have been specific cases where patients have received over 100 drug doses per day. The phenomena of such critically ill patients taking such a large number of medication doses per day has created acceptance of the practice termed "polypharmacy".

These large numbers of drug doses create an increased risk of medication errors, the consequences of which are often totally unforeseen. In treating a critically ill patient the clinician must assume that the drugs can be, and are in fact administered at the prescribed times, and at the prescribed infusion rates and that the drugs are compatible with one another. In the past, clinicians have generally assumed that the mixing within an intravenous line is minimal and that back-to-back solutions administered sequentially through the same intravenous line move through the line with a minimal interface, and therefore little if any reaction, between them.

Recent studies have shown that this is an incorrect assumption. There is substantial mixing as two fluids pass down an intravenous line, even sequentially. This mixing raises important issues on potential clinical problems in drug administration and drug-drug compatibilities in the practice of polypharmacy. In cases where no compatibility information is available, additional intravenous catheters are generally placed in the patient through which additional drugs are delivered, thus increasing the risks for contamination and sepsis in these already compromised patients. Alternatively, the risk is taken that the drugs are compatible and they are infused continuously, or sequentially down the same line.

The issues of multiple intravenous lines, contamination of lines and medication errors have created the need for automation to meet the increasing demand to administer these multiple drug doses. All of this only serves to further highlight the substantial need for vastly expanded information relating to physical compatibility and fluid mixing to enable clinicians to correctly and safely prescribe and administer the multiple doses of multiple drugs. Until all of these needs are met, the quality of care to patients is reduced, compromised and even at times inadequate and life threatening.

Currently in medical practice, there are about 300 unique drugs available for intravenous administration to patients. This number rapidly increases if one includes the various manufacturers' formulations for each drug and the various solutions and diluents available. When assessing compatibilities during the short-term mixing that occurs during intravenous drug administration, the focus is primarily on physical compatibility as related to solubility and/or precipitates because of the potentially devastating effects of intravenous particles.

From the fact that there are about 300 unique drugs currently available, one can readily calculate that, if one limits his concern to combinations of two drugs only, there are about 45,000 unique combinations for which physical compatibility data is necessary to complete the dataset for a given diluent such as 0.9% saline. Furthermore, the order of addition of multiple drugs to a solution can effect the result and therefore each combination of drugs must be tested in all possible orders of addition. This consideration brings to about 90,000 the number of physical compatibility tests necessary to complete an entire matrix of data for a given diluent when testing all possible two drug combinations of the 300 unique drugs to be considered. As can be appreciated, when combinations of three or more drugs are considered, this number increases exponentially. Similarly, the number goes up dramatically when one takes into account the various manufacturers' formulations for each given drug. One might also be legitimately concerned with the various dosages available for each drug. Additionally, there are two major diluents for intravenous drugs, 5% dextrose in water and 0.9% saline in water, and for completeness, each combination should be evaluated in a mixture of these two major diluents and at least a 50/50 combination of the two.

Our number therefore grows to about 270,000 drug-drug physical compatibility tests which are required, still limiting ourselves to only two-drug combinations, to complete the dataset matrix to supply the modern physician with a complete and relevant database from which multiple intravenous medications can be safely and effectively prescribed and administered.

The reference book, Handbook on Injectable Drugs, by Lawrence Trissel, is a compilation of all compatibility information published over the last 30 years. It has over 700 pages, summarizes essentially all of the published data on inter-drug compatibility and is the most cited reference source for drug and solution compatibility information. The Handbook contains the results of about 15,000 compatibility tests, the fruits of over thirty years of work. Therefore, over the last thirty years, less than 10% (15,000) of the possible combinations have been tested and reported. The amount of necessary information that is missing from the published literature available to the medical profession is staggering.

Not only is the published state of the art sorely incomplete, but the methodology used to generate the results in the published literature is not standardized (not a USP test), is totally subjective (visual observations) and performed manually. Additionally, some of this testing is out of date or not applicable to today's advanced infusion techniques. For example, a current focus is on Y-site injection of drugs rather than premixing in a reservoir, a technique not considered in the prior art methods of gathering inter-drug compatibility data.

There are other issues which must also be considered if the data upon which the physician relies is to be trustworthy. These include such considerations as whether the drug was tested at too dilute a concentration for the proposed application or for non-relevant time period(s) and under conditions not relevant to those under which the drug would generally be administered. For example, such data has traditionally been collected by the prior art manual and subjective means after the drugs had been in contact with each other for at least 24 hours and in whatever container and/or quantities the researchers chose, which were often quite arbitrary. However, in current intravenous practice, unless intentionally so, particular quanta of two drugs are rarely if ever in contact with each other for more than a matter of minutes, and then in very small quantities within the lumen of the IV tube.

In 1987-88, Dasta et al. began to reassess the issue of drug compatibility (Dasta, et al., Comparison of Visual and Turbidimetric Methods for Determining Short-Term Compatibility of Intravenous Critical-Care Drugs, American Journal of Hospital Pharmacy, vol. 45, pp 2361-2366, Nov. 1988). The stated motivation for the study was the fact that the current literature on compatibilities is largely based on studies that used methodologies that do not apply to the ICU environment. It was recognized that rarely is there any information that is specifically applicable to this situation. In an attempt to standardize and semi-automate the laborious procedures historically employed, he designed a study to re-evaluate the short-term compatibility of 45 previously considered "incompatible" drug-drug combinations under more relevant conditions and to compare the historical, non-standardized visual observations with the absorbance changes due to turbidity as recorded by a spectrophotometer.

He found that about 50% of the previously listed "physically incompatible" combinations, were in fact compatible when tested under conditions relevant to the ICU. Additionally and interestingly, the turbidity measurement using spectrophotometry was not reliable as it was unable to consistently detect changes that were observed visually. The author concludes that detection may require a more sophisticated instrument and that perhaps other techniques could be developed to overcome the inadequacies of this system. Given that there was no alternative automated process adapted to ascertain physical compatibility of drugs, it was estimated that even with his ability to speed-up the subjective, laborious, visual test system of the prior art, it would take a group about 41 years to complete the database of relevant information on physical drug compatibility in two solution vehicles.

Since that time, a number of automated test systems for various applications other than physical compatibility of drugs have been developed. One such alternative automated detection method is disclosed in U.K. Pat. No. 2,030,696. The essence of this disclosure is a semi-quantitative mathematical algorithm for detecting the appearance or disappearance of color or turbidity using serial dilutions examined over an absorbance range. Another detection method is disclosed in Research Disclosure *17543 (November, 1978), which includes modifying a spectrophotometer to measure haze in beverage bottles. The system does not detect precipitation.

Another device and method is disclosed in WO86/07454. This publication discloses a particular apparatus for determining color and turbidity in which light collected after traversing a sample is chromatically dispersed and the intensity of each of the components of the dispersion is measured. The apparatus and method disclosed are used for the control of transportation of liquid oil through pipelines.

U.S. Pat. No. 4,108,602 discloses an automated sample changing system for chemical analysis. It transports the samples to and from an analysis apparatus, such as a UV spectrophotometer. U.S. Pat No. 4,678,326 discloses an apparatus for measuring various optical properties of a liquid sample. U.S. Pat. No. 4,497,898 discloses a method for detecting both the protein and fat content of milk simultaneously, which method employs, intelalia, color developing reagents and simultaneous multiple single source light beams. However, the method disclosed in this reference is incapable of detecting precipitation. U.S. Pat. No. 4,429,373 describes a system for the spectrophotometric analysis of blood for its constituents.

SUMMARY OF THE INVENTION

The shortcomings in the prior art with respect to the need for valid, complete and relevant reference information on the physical intercompatibility of chemicals, and especially drugs, in solution are met by the present invention which is an automated, high volume process for evaluating the physical compatibility of two or more chemicals in solution. The method includes mixing the chemicals in solution in predetermined relative quantities under particular predetermined conditions and reading the absorption of light of the resulting solution to detect, identify and quantify changes in physical properties caused by the mixing of the chemicals in solution. The absorption is read preferably at at least two wavelengths.

The method of the invention further includes testing the intercompatibility of the chemicals under conditions identical or as close as possible to those conditions under which the chemicals will be employed for their intended purposes. Such conditions may include controlling the time that the chemicals to be tested are in actual contact with one another to simulate the actual amount of time that the chemicals will in fact be in contact with one another in the real life application, such as in an intravenous line. These conditions might also include the relative quantities of the chemicals in contact with one another. Another factor could well be the size and material of the container in which the solutions are contained during testing.

Moreover, the process includes testing solutions of combinations of chemicals in which the chemicals have been added to the solution in all possible orders of addition; i.e. adding chemical A to solution, then adding chemical B to the solution, then performing all tests; then preparing another solution to be tested by putting chemical B in solution, then adding chemical A to the solution, then repeating the tests. In this way, the method allows for order-dependent reaction&, which have traditionally been ignored in the prior art. As the reader will appreciate, the method of the invention is readily employed to ascertain the intercompatibility under real life conditions of solutions containing any number of chemicals.

The invention also provides a system for evaluating the physical compatibility of two or more pharmaceutical chemicals in solution. The system comprises fluid conveyance means for conveying at least first and second chemicals in solution. The system also includes a test well and fluid mixing means communicating with the fluid conveyance means for mixing the chemical solutions in predetermined relative quantities in the test well. The system includes measurement means for measuring the absorption of the mixture and output means for displaying the absorption measurements. Control means operates the measurement means and output means (i) to measure the absorption of the mixture at a first wavelength within the visual spectrum in the range of 400 to 500 nm to detect both changes in color and changes in physical properties caused by mixing of the chemical solutions; (ii) to operate the measurement means to measure the absorption of the mixture at a second wavelength above the visual spectrum in the range of 610 to 650 nm to detect only changes in physical properties caused by mixing of the chemical solutions; (iii) to compare the absorption measured at the first wavelength with the absorption measured at the second wavelength to differentiate between solely color changes and physical property changes (with or without color changes) caused by the mixing; and (iv) to display the differentiated results.

BRIEF DESCRIPTION OF THE DRAWINGS

FIG. 2 is a schematic representation of one exemplary configuration of a 96 well microtiter plate on which various combinations of two drugs each are mixed for physical compatibility evaluation in accordance with the present invention;

FIG. 3 is a schematic representation of a second exemplary configuration of a 96 well microtiter plate on which various combinations of two drugs each are mixed for physical compatibility evaluation in accordance with the present invention.

DETAILED DESCRIPTION OF THE INVENTION

The present invention provides an automated, high volume process for evaluating the physical compatibility of chemicals in solution. More specifically, this invention pertains to the automated, reproducible, quantitative measurement of any physical aberration which results from two or more drugs coming into contact with each other in solution. Such aberrations may take the form of, for example, color formation and/or change, the formation of turbidity, haze, precipitate, crystals or globules resulting from mixing at least two chemicals in predetermined quantities in solution. The drugs and solutions are prepared under the same conditions as are generally contemplated for administration in the hospital or, more particularly, the ICU.

The present invention allows the medical community to be provided with complete and relevant physical compatibility information for use in improving patient care in the practise of administering two or more intravenous drugs, solutions or chemicals continuously or sequentially. This information was heretofore otherwise difficult or impossible to generate in a reasonable time frame because the existing test methods were manual, non-standardized, extremely time consuming, laborious, and subjective.

Referring now to FIG. 1, there is presented a matrix graphically indicative of the amount of clinically relevant information missing from the published literature. Down the left hand margin are listed 48 of the most commonly prescribed injectable drugs. Each is numbered sequentially. Along the top of the chart are numbers corresponding to those same drugs so that information on a given combination of these drugs is contained in the appropriate box at the intersection of lines drawn between the desired combination on the horizontal and vertical axes.

The boxes containing a "C" or "I" represent drug combinations for which the indication "Compatible" or "Incompatible" is found in the published literature. Empty boxes represent combinations for which no information on physical compatibility is available in the published literature. This information is reported in the Trissel reference discussed above. The boxes containing an "X" represent combinations which have been tested by the inventors using the method of the present invention over a period of nine months. In fact, in the same nine months, the inventors, using the method of the present invention, have collected a volume of data results of approximately 15,000 tests, equivalent to the entire volume of data reported in the Trissel handbook, which was collected over 30 years.

It is anticipated that the first full database to be generated will be approximately seven times as large as Trissel's and include tests of all two-drug combinations of about 250 unique drugs in three diluents, 0.9% saline, 5% dextrose and a solution mixture of the two. The inventors estimate that the additional tests necessary to complete the first full database could be completed in 2–3 years with the method and apparatus of the present invention.

Figure 1A:
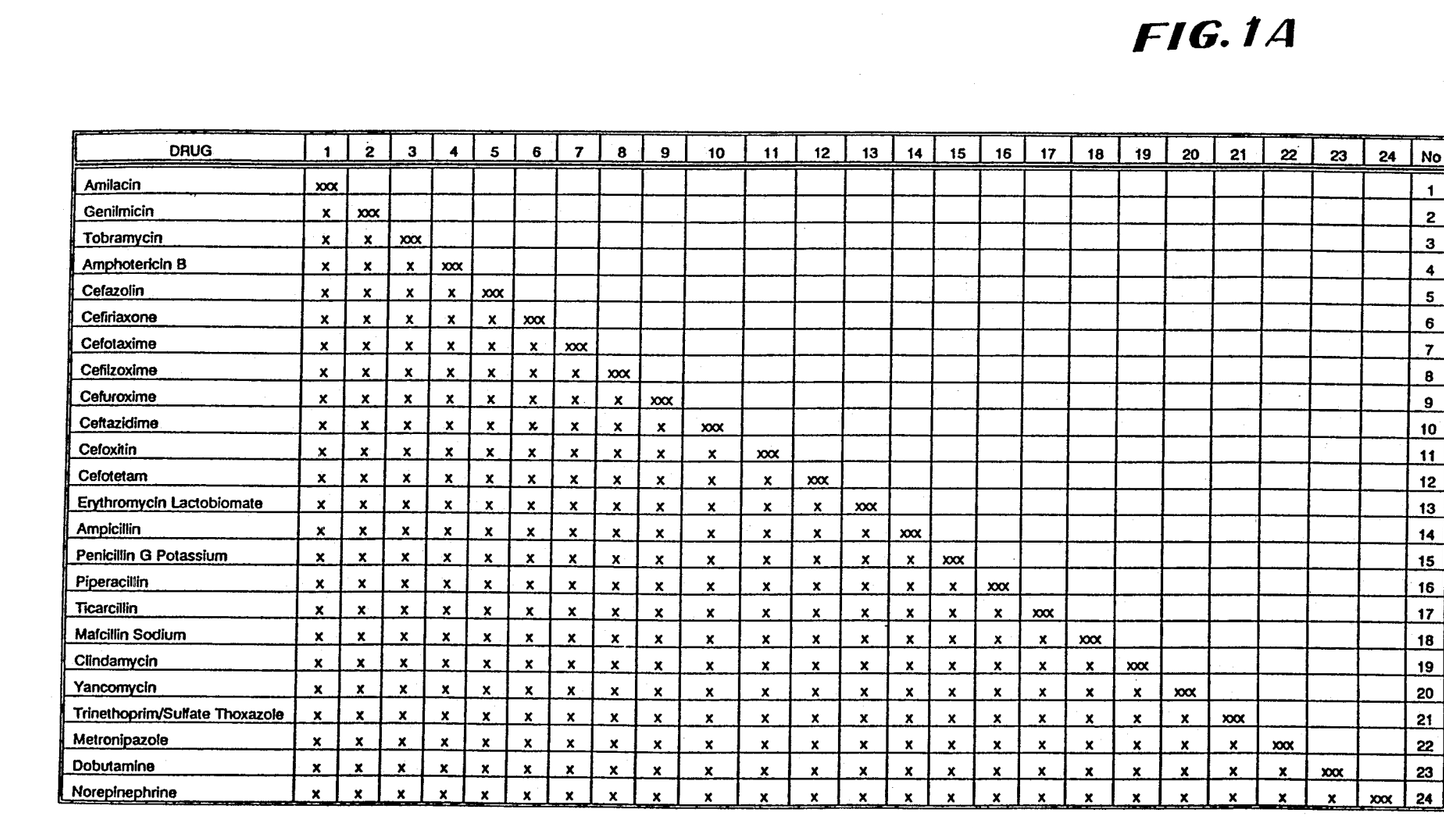
FIGS. 1A–1B are a matrix comparison of information available from the published prior art and information generated by the method of the present invention.
Figure 1B:
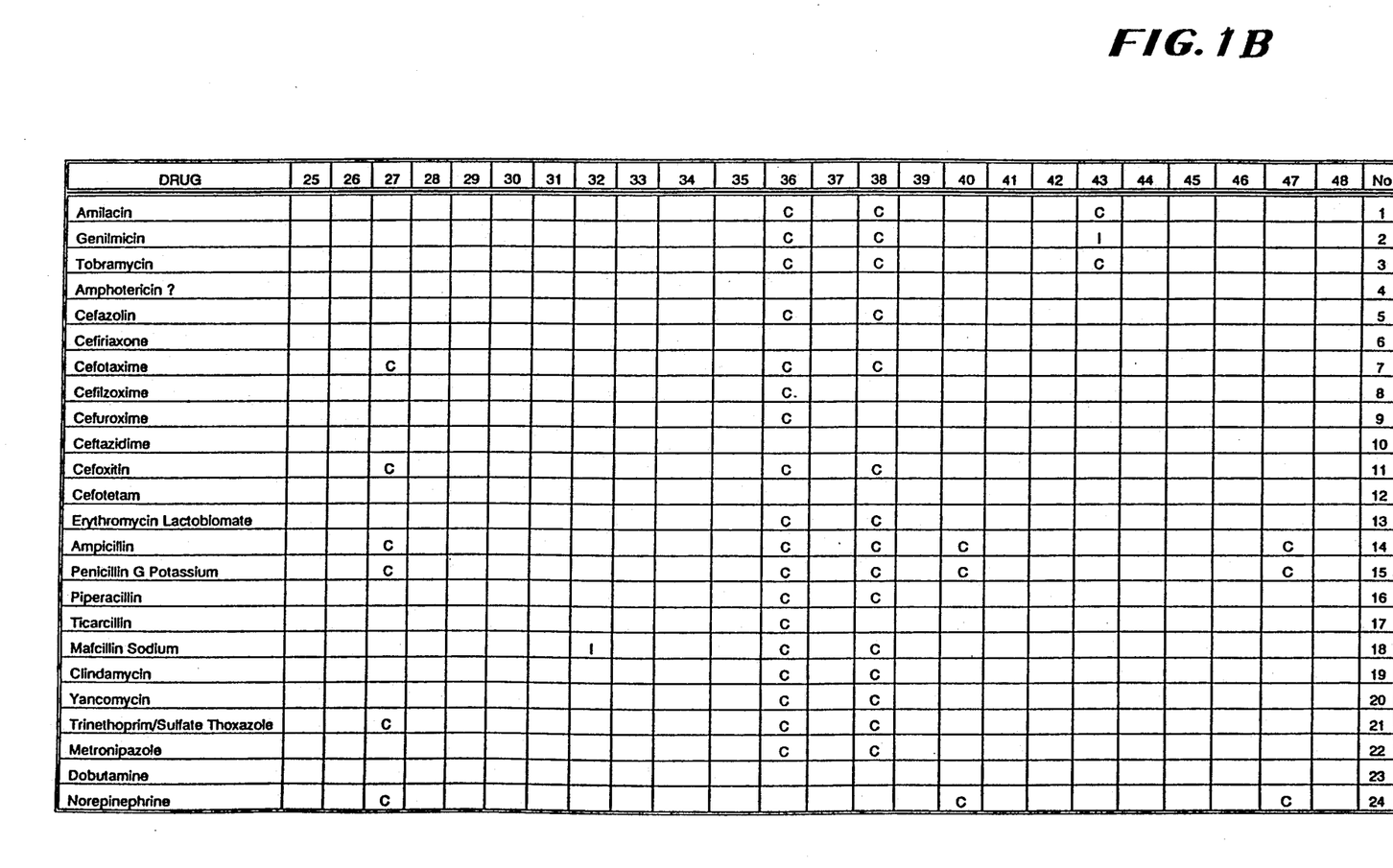
Figure 1C:
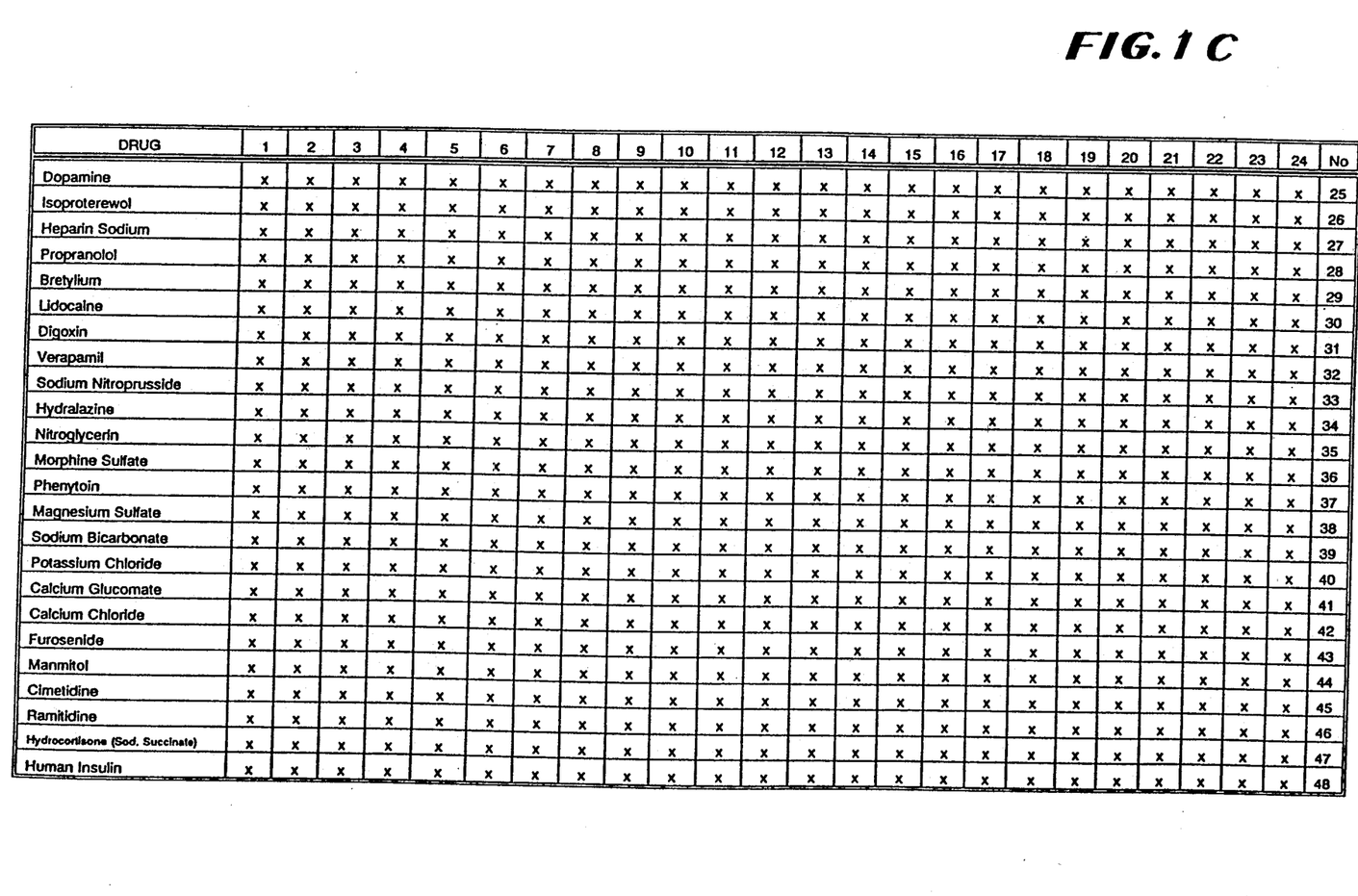
Figure 1D:
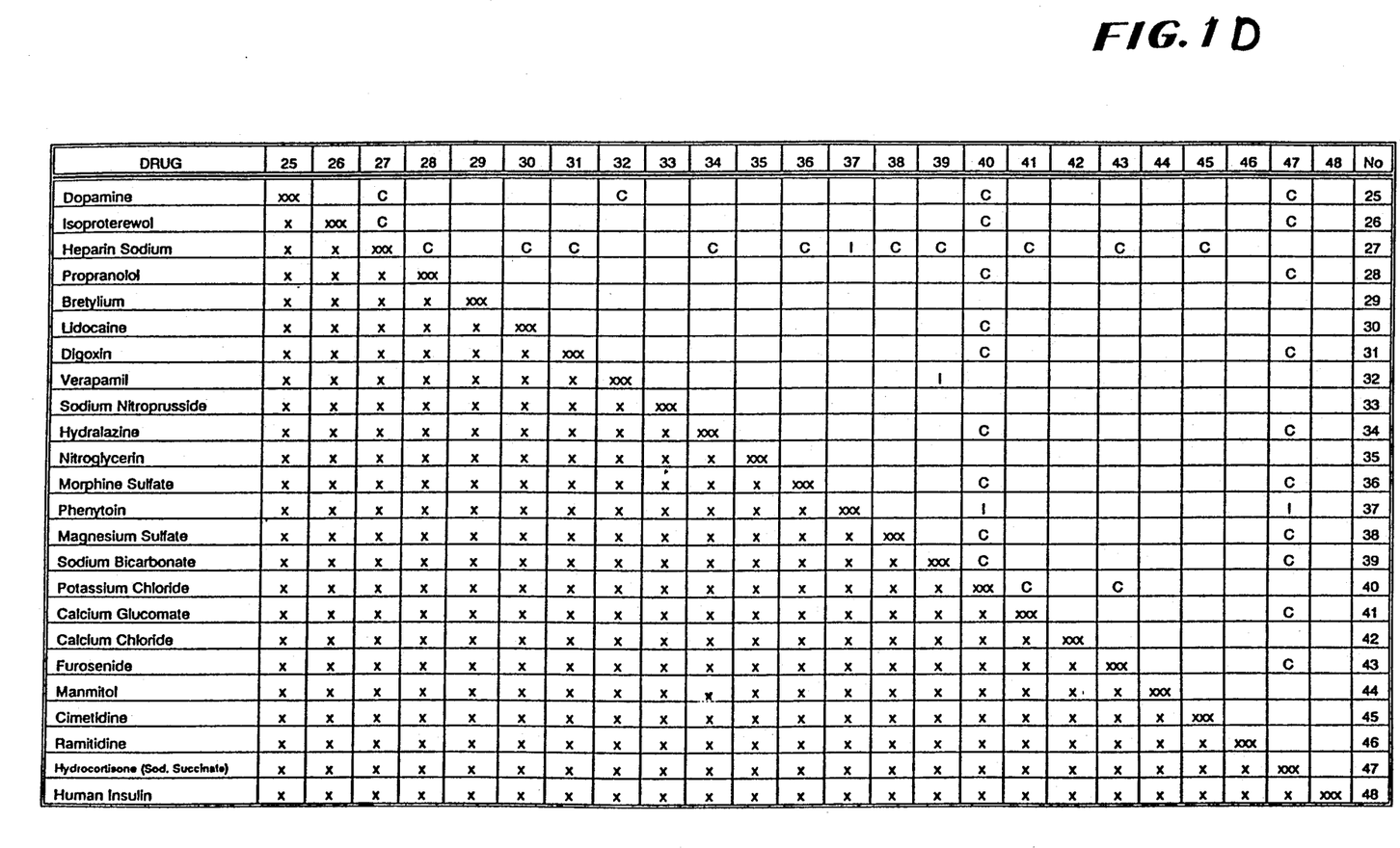
Figure 4:
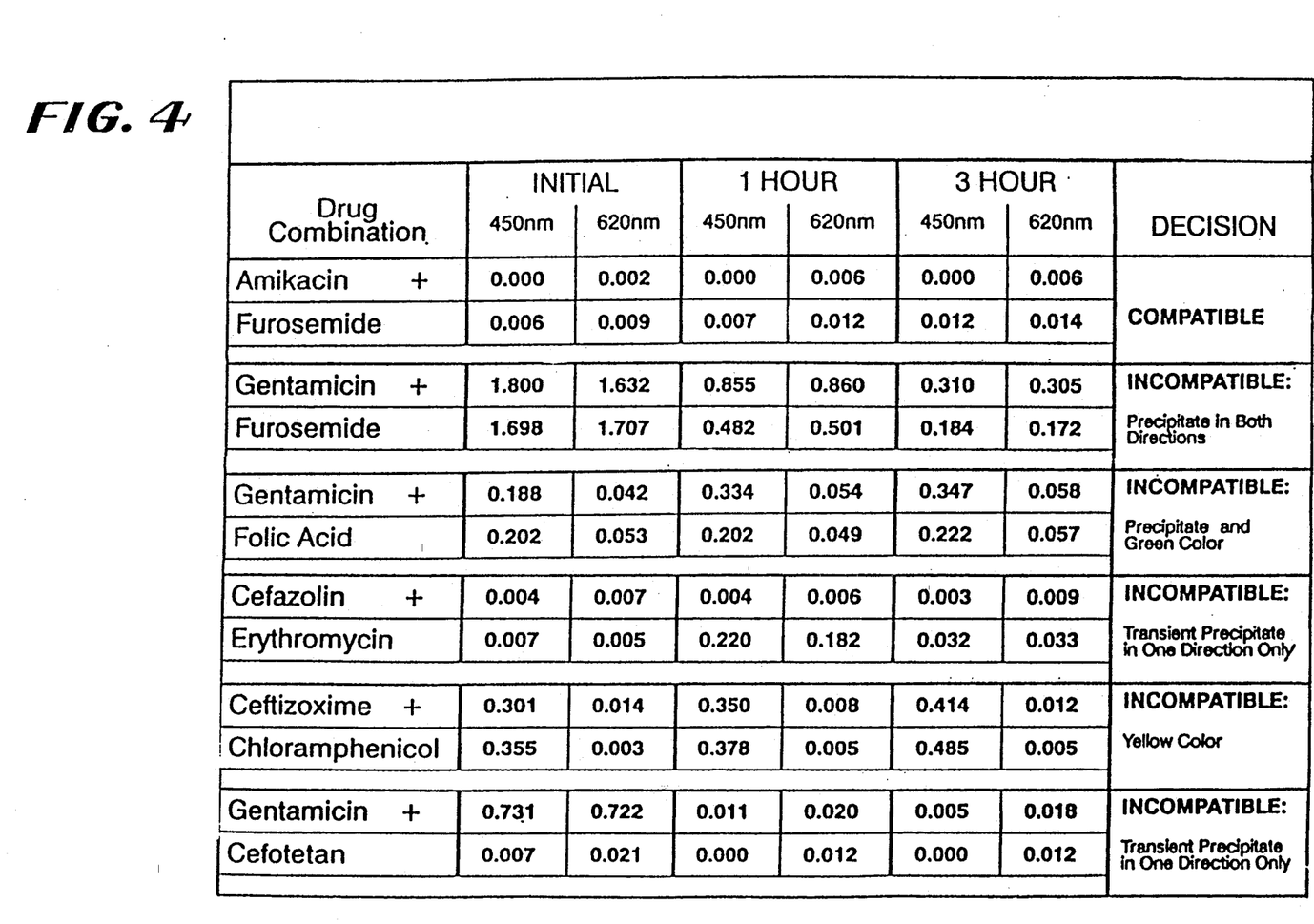
FIG. 4 is a chart of exemplary results derived by the method of the present invention.
Figure 5:
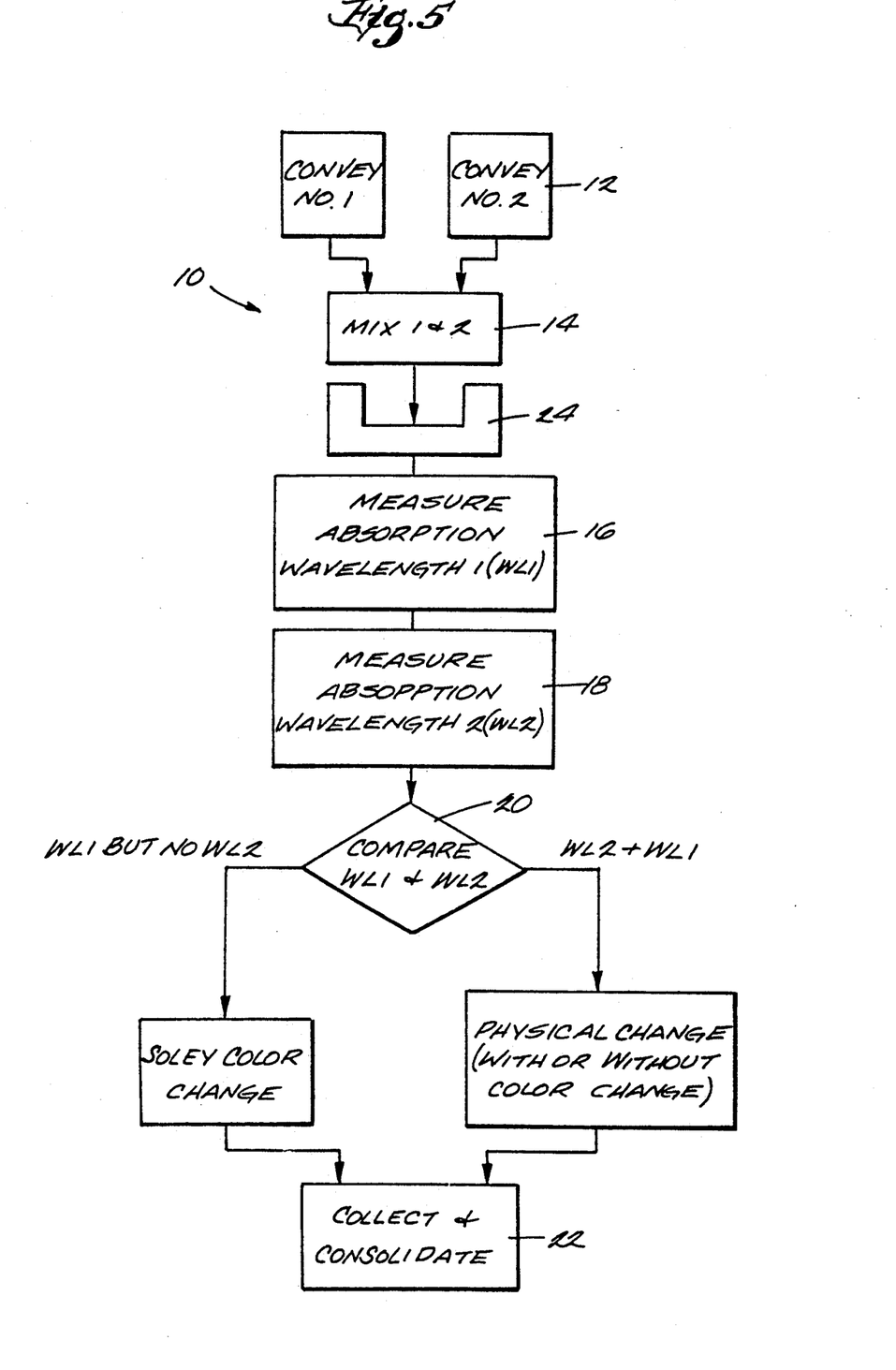
FIG. 5 is a schematic view of a system that embodies the features of the invention.

The process of the present invention is made possible by combining specialized microtiter plate instrumentation and customized application computer programs. The system 10 that embodies the features of the invention is shown in schematic form in FIG. 5. The system 10 includes first through sixth means, respectively 12, 14, 16, 18, 20 and 22, for carrying out the test procedure as previously described. The first means 12 serves to convey at least first and second chemicals in solution to the second means 14, where the chemical solutions are mixed in predetermined relative quantities in a test well 24. The third means 16 measures the absorption of the mixture at a first wavelength within the visual spectrum in a range of 400 to 500 nm to detect both changes in color and changes in physical properties that may be caused by mixing the chemical solutions. The fourth means 18 measures the absorption of the mixture at a second wavelength above the visual spectrum in a range of 610 to 650 nm to detect only changes in physical properties that may be caused by mixing the chemical solutions. The fifth means 20 compares the absorption measured at the first wavelength with the absorption measured at the second wavelength to differentiate between solely color changes and physical property changes (with or without color changes) caused by the mixing. The sixth means 22 collects and consolidates the differentiated results generated by the fifth means 20. FIG. 4 is an example of these collected and consolidated results. In the preferred embodiment, each chemical or drug solution is mixed with a second chemical or drug solution in a predetermined ratio. The inventors employed the BioMek® 1000 Automated Laboratory Workstation (Beckman Instruments, Inc.) in the 96-well microtiter plate configuration for this purpose. Examples of two types of programmed mixing configurations are shown in FIGS. 2 and 3.

FIG. 2 is a schematic representation of one exemplary and preferred configuration of a 96 well microtiter plate on which various combinations of two drugs are mixed for physical compatibility evaluation in accordance with the invention. In FIG. 2, eight chemical solutions, all in the same single diluent, such as 0.9% saline, are mixed with each other in all possible combinations and in both orders of addition, in the wells of the microtiter plate.

Immediately after mixing, and at one or more predetermined time periods, the absorbance of the microtiter plate wells are read preferably at two or more wavelengths, one of which is chosen to detect color changes. Such a wavelength, due simply to the array of the visible spectrum, is in the range of 400 to 500 nm. The inventors have determined empirically that the preferred wavelength at which to read the plates for color change is approximately 450 nm. At this wavelength, the presence or absence and/or change in physical properties such as haze, turbidity, precipitation, crystals or globules will also be detected.

In the preferred embodiment, the plates are also read a second time at a second wavelength. For this second reading, a second wavelength in the vicinity of 610 nm to 650 nm, and preferably 620 nm is chosen. This second reading at 620 nm adds an additional and particularly advantageous dimension to the present invention over the prior art. More specifically, at 450 nm, both color and the physical changes described above are detected and quantified. However, at 450 nm these parameters are not differentiated from one another. In the vicinity of 620 nm, the physical changes are detected and quantified but color is not. Therefore, the reader will appreciate that certain inferences may be drawn from a combination of the readings, or the lack thereof, at the two wavelengths. Specifically, if a reading is obtained at 450 nm but none is obtained at 620 nm, the phenomena being detected must be one of color only, since otherwise, a reading at 620 nm would have been obtained. Similarly, if a reading is obtained at both 450 and 620 nm, the presence of a physical change such as turbidity, etc. is confirmed.

In conjunction with the above, it must be noted that the ability to differentiate between changes in color versus changes in turbidity, etc. is crucial to the medical professional. This is because some given amount of color or color change is generally considered clinically acceptable in injectable drugs.. However, a far smaller degree of haze, turbidity, precipitation, etc. is acceptable in injectable drugs. Therefore, one will appreciate that it is absolutely essential for the achievement of meaningful information to not only detect and quantify the presence or magnitude of the variable, but to identify and differentiate it as a physical or color phenomenon. Only by performing readings at at least two different wavelengths, preferably in the vicinities of 450 and 620 mm, can such differentiation be accomplished.

The microtiter plate wells may be read using a computer-driven EAR 400-AT Automated Microplate Reader (SLT Labinstruments GmbH, Salzburg, Austria) or similar apparatus. The time periods are chosen to coincide with the estimated lengths of time that the particular combination of drugs being tested are expected to be in contact with one another during actual administration conditions.

Each combination of two or more chemicals is analyzed at least twice, alternating the order in which they are mixed. Appropriate blanks for each chemical combination are also measured including vehicle or diluent only, each chemical plus vehicle, and each chemical plus itself. The change or residual absorbance for each chemical combination at each wavelength and time period are calculated by computer by subtracting out the appropriate blanks. These residual absorbance are then used to evaluate the physical compatibility for each chemical combination.

More specifically about the blanks, the microtiter plate matrix of FIG. 2 includes columns with chemicals other than those specifically to be tested against one another. These are the various controls. For example, in FIG. 2, columns 1 and 2 represent controls with vehicle, or diluent, only and a single chemical plus diluent, respectively. These samples are run to determine baseline values which are subtracted from readings obtained from the drug combination samples to determine the change, presence or absence of the phenomena being measured from the single drug condition. Column 11 represents quality control samples to determine acceptability of the microtiter plate run. These quality control samples have known readings which should be obtained at 450 and 620 nm if the apparatus is functioning properly.

The automated test system of the invention has been validated against the manual, subjective, visual method. All microtiter plates are prescreened for aberrant wells and unacceptable plates are discarded. Two types of quality control (QC), represented by the samples in column 11 in FIG. 2, are also included on each microtiter plate as a check for accuracy, precision and reproducibility over time. The first type of QC is the actual formation of turbidity monitored when six different concentration levels of silver nitrate and sodium chloride solutions are mixed in diluent. These are represented by the first 6 boxes in column 11 of FIG. 2.

The second QC is the direct measurement of stable latex particles in suspension (0.300 microns), in duplicate. These are represented by the last 2 boxes in column 11 of FIG. 2. Quality control results from each plate are reviewed for acceptance of the microtiter plate run and the establishment and evaluation of trends and empirical results falling outside an accepted limit, such as two standard deviations.

Another important feature of the present process is that the chemicals being tested are tested under conditions relevant to those under which they will most probably be employed or administered. For example, as noted above, in the prior literature, drugs being tested for physical intercompatibility were often left in contact with one another for 24 or even 48 hours. After this long period of time, evidence of incompatibility was often found. However, today drugs are virtually never in contact with one another for more than a matter of minutes or perhaps a few hours when being administered to a patient.

The inventors have discovered that many combinations previously rated incompatible with one another in the prior literature are in fact compatible under the conditions and for the time periods that they are in contact with one another during normal administration. These conditions may include not only time in contact with one another, but relative quantities, order of mixing, and even the size and material of the container or conduit through which the drugs are administered, such as PVC or non-PVC tubing. The process of the present invention is intended to allow for all such conditions by employing appropriate containers and controlling the relative quantities and time of mixing, etc. to simulate as much as possible actual administration conditions. For example, it is contemplated that readings will be preferably taken at initial mixing (i.e. within 5 minutes), at 1 hour and 3 hours and it such other times as might be dictated by the particular drugs being tested. Additionally, each drug solution can, prior to testing, be pumped through intravenous tubing, such as PVC or silica, to simulate contact time during intravenous therapy and add any tubing leechables to the solutions which may have an effect on the drug intercompatibilities.

FIG. 3 is a representation of a second embodiment of a configuration of a 96 well microtiter plate on which various combinations of two drugs each are mixed for physical compatibility evaluation. Unlike the embodiment of FIG. 2, in which each of eight drugs were tested against each other, the embodiment of FIG. 3 contemplates testing each of eight drugs (numbered 1 through 8) against each of eight other drugs (numbered 9 through 16). In this embodiment therefore, there are 64 individual combinations on each plate and a total of 128 individual test samples when one tests for both orders of addition of the solutions on the two plate runs. The tests are conducted as described above with respect to FIG. 2.

In FIG. 3, columns 1, 2 and 12 represent blanks (i.e. pure diluent or single drugs in solution) for calculation purposes. Column 11 of FIG. 3 again represents quality control. The samples of these columns are similar in design and function to those similarly functioning samples described above with respect to FIG. 2.

Examples of results obtained by the present method for individual chemical combinations are shown in FIG. 4. The automated test system and method of the present invention, when compared to the currently accepted visual test system method, improves accuracy, precision and reproducibility. An examination of FIG. 4 illustrates some of the heretofore unknown, and often unconsidered, information now made readily available by the present invention. In the chart for each drug combination, the values on the upper horizontal line represent values calculated when the top listed drug solution of the pair was added to the microtiter plate well first. The lower horizontal line for each drug solution pair represents values calculated when the lower listed drug was added to the well first.

For example, the reader's attention is directed to the readings under "Initial" for the combination of ceftizoxime and chloramphenicol. From the reading at 450 nm (0.301 and 0.355) we know that there is a significant change in either color and/or turbidity or other physical property, as described above. However, the relative lack of readings, in either direction, at 620 nm tells us that there is no turbidity or precipitation, and the change observed is, therefore, one of color only. Additionally, one can ascertain that the degree of color change increases over time regardless of the order of mixing.

The importance for testing drug combinations in each order of addition is exemplified by the last combination in FIG. 4 of gentamicin and cefotetan. When cefotetan is added to gentamicin in solution, an initial (within about 5 minutes of mixing) and very significant reaction is observed. Because of the existence of readings at both 450 and 620 nm, we cannot tell whether the change is in physical property or both color and physical property, but we do know that there is at least a change in physical properties. However, note that in the reverse situation, when gentamicin solution is added to cefotetan solution, no significant reaction is observed. Furthermore, from the data, one can infer from the relative lack of readings after 1 hour and 3 hours that an initial substantial haze goes back into solution after a period of time.

Because of the automation and computerization, the present test system has a minimum increase in productivity of the order of 20-fold. This means that at the very least a years amount of work can now be completed in 2 to 3 weeks or less. Any new chemical or drug solution can be evaluated for meaningful physical compatibility with all other relevant drugs in about 6 weeks. With the present invention, the medical community can reasonably expect a complete and relevant informational database for the 300 intravenous drugs currently available, tested in 3 different vehicles, to be available within 2 years.

We claim:

1. A system for evaluating the physical compatibility of two or more pharmaceutical chemicals in solution comprising:
   a test well;
   fluid conveyance means for conveying at least first and second chemicals in solution;
   fluid mixing means communicating with the fluid conveyance means for mixing the chemical solutions in predetermined relative quantities in the test well;
   measurement means for measuring the absorption of the mixture in said well;

output means for displaying the absorption measured by the measurement means; and control means for operating the measurement means and output means (i) to measure the absorption of the mixture at a first wavelength within the visual spectrum in the range of 400 to 500 nm to detect both changes in color and changes in physical properties caused by mixing of the chemical solutions; (ii) to measure the absorption of the mixture at a second wavelength above the visual spectrum in the range of 610 to 650 nm to detect only changes in physical properties caused by mixing of the chemical solutions; (iii) to compare the absorption measured at the first wavelength with the absorption measured at the second wavelength to differentiate between solely color changes and physical property changes caused by the mixing; and (iv) to display the results of the comparison.

* * * * *